United States Patent [19]

Balasubramanyan et al.

[11] Patent Number: 4,605,747

[45] Date of Patent: Aug. 12, 1986

[54] α-BENZYL-α-TRIAZOLYL PINACOLONE COMPOUNDS

[75] Inventors: Sugavanam Balasubramanyan, Vienna, Austria; Margaret C. Shephard, Maidenhead, England

[73] Assignee: Imperial Chemical Industries PLC, London, England

[21] Appl. No.: 765,147

[22] Filed: Aug. 13, 1985

Related U.S. Application Data

[60] Continuation-in-part of Ser. No. 60,166, Jul. 24, 1979, abandoned, which is a continuation of Ser. No. 879,872, Feb. 21, 1978, abandoned, which is a continuation-in-part of Ser. No. 866,063, Dec. 30, 1977, abandoned, which is a division of Ser. No. 718,207, Aug. 26, 1976, Pat. No. 4,079,143.

[30] Foreign Application Priority Data

Aug. 26, 1975 [GB] United Kingdom ............... 35208/75
Sep. 10, 1975 [GB] United Kingdom ............... 37241/75
Jul. 2, 1976 [GB] United Kingdom ............... 27649/76

[51] Int. Cl.⁴ .................. A01N 43/653; C07D 249/08
[52] U.S. Cl. ......................... 548/262; 71/76; 71/92
[58] Field of Search ......................... 548/262

[56] References Cited

U.S. PATENT DOCUMENTS

| | | | |
|---|---|---|---|
| 3,658,813 | 4/1972 | Godefroi et al. | 548/341 |
| 3,755,349 | 8/1973 | Timmler et al. | 548/399 |
| 3,872,117 | 3/1975 | Meiser et al. | 548/262 |
| 3,897,438 | 7/1975 | Draber et al. | 548/262 |
| 3,912,752 | 10/1975 | Meiser et al. | 548/262 |
| 3,952,002 | 4/1976 | Kramer et al. | 548/262 |
| 4,005,083 | 1/1977 | Buchel et al. | 548/101 |
| 4,073,925 | 8/1976 | Sugavanam et al. | 548/336 |
| 4,147,793 | 4/1979 | Shephard et al. | 548/341 |
| 4,243,405 | 1/1981 | Sugavanam et al. | 514/383 |

FOREIGN PATENT DOCUMENTS

| | | | |
|---|---|---|---|
| 2431407 | 1/1976 | Fed. Rep. of Germany | 548/262 |
| 754111 | 4/1976 | South Africa | 548/262 |
| 1244530 | 9/1971 | United Kingdom | 548/341 |
| 1364952 | 8/1974 | United Kingdom | 548/262 |

*Primary Examiner*—Alton D. Rollins
*Attorney, Agent, or Firm*—Cushman, Darby & Cushman

[57] ABSTRACT

The compounds of the formula (I):

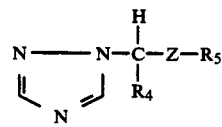

wherein $R_4$ is hydrogen, $C_{1-6}$ alkyl, alkenyl or alkynyl having up to 4 carbon atoms, phenylallyl, phenyl, benzyl optionally ring-substituted with for example halogen, $C_{1-4}$ alkyl or alkoxy, nitro, trifluoromethyl, cyano or methylene-dioxy, of alpha-($C_{1-4}$ alkyl) benzyl optionally ring-substituted with for example halogen, and $R_5$ is $C_{1-6}$ alkyl or cycloalkyl having up to 6 carbon atoms; and Z is C=O or a derivative thereof; or salts of such compounds. The compounds have fungicidal and plant growth regulating properties.

5 Claims, No Drawings

α-BENZYL-α-TRIAZOLYL PINACOLONE COMPOUNDS

This application is a continuation-in-part of Ser. No. 60,166 filed July 24, 1979 which was in turn a continuation of Ser. No. 879,872, filed Feb. 21, 1978, now abandoned, which was a continuation-in-part of Ser. No. 866,063, filed Dec. 30, 1977, now abandoned, which was a divisional application of Ser. No. 718,207, filed Aug. 26, 1976, now U.S. Pat. No. 4,079,143.

The invention relates to heterocyclic compounds which are 1,2,4-triazole compounds, to compositions containing them, to methods of combatting pests (particularly fungal pests) using them and to methods of regulating plant growth using them.

The compounds have the general formula (I):

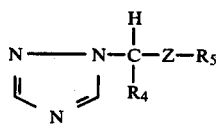

wherein $R_4$ is hydrogen, $C_{1-6}$ alkyl, alkenyl or alkynyl having up to 4 carbon atoms, phenylallyl, phenyl, benzyl optionally ring-substituted with for example halogen, $C_{1-4}$ alkyl or alkoxy, nitro, trifluoromethyl, cyano or methylene-dioxy, of alpha($C_{1-4}$ alkyl) benzyl optionally ring-substituted with for example halogen, and $R_5$ is $C_{1-6}$ alkyl or cycloalkyl having up to 6 carbon atoms; and Z is C=O or a derivative thereof; or a fungicidal salt of such a compound.

The compounds can contain chiral centre(s). Normally the compounds are prepared in the form of racemic mixtures. However these and other mixtures can be separated into the individual isomers by methods known in the art.

The halogen can be fluorine, chlorine, bromine or iodine while the alkyl group can be one of the groups listed below for $R_4$.

Suitable C=O derivatives are ketals, hydrazones, semicarbazones, imines and oximes.

The alkyl groups, which can be straight or branched chain, preferably have 1 to 5 carbon atoms; examples are methyl, ethyl, propyl (n- or i-propyl) and buty (n-, i- or t-butyl). Suitable alkenyl and alkynyl groups (which can also be straight or branched chain) are allyl and propargyl.

The benzyl group can be substituted in its $CH_2$ and/or phenyl moieties. Suitable substituents on its phenyl moiety are halogen, $C_{1-4}$ alkyl [e.g. methyl, ethyl, propyl (n- or i-propyl) and butyl (n-, i- or t-butyl)], halo-($C_{1-4}$ alkyl), phenyl, halophenyl (e.g. chlorophenyl), cycloalkyl, nitro, cyano, hydroxy, $C_{1-4}$ alkoxy (e.g. methoxy or ethoxy), ($C_{1-4}$ alkylene)dioxy (e.g. methylenedioxy), ($C_{1-4}$ alkoxy) ($C_{1-4}$ alkyl) [e.g. 2-methoxy- or ethoxy-ethyl], mercapto, ($C_{1-4}$ alkyl) thio [e.g. methyl- or ethyl-thio], ($C_{1-4}$ alkyl) sulphonyl [e.g. methyl- or ethyl-sulphonyl], ($C_{1-4}$ haloalkyl) sulphonyl [e.g. trifluoromethylsulphonyl], phenyl-sulphonyl, unsubstituted or mono- or di- ($C_{1-4}$ alkyl) substituted sulphamoyl or carbamoyl, carboxy, ($C_{1-4}$ alkoxy)- carbonyl [e.g. methoxy- or ethoxy-carbonlyl], unsubstituted or mono- or di- ($C_{1-4}$ alkyl) substituted amino, ($C_{1-6}$ alkanoyl) amino, N-($C_{1-4}$ alkyl)-substituted ($C_{1-6}$ alkanoyl)-amino, formylamino, N-($C_{1-4}$ alkyl)-substituted formylamino, phenylethyl, phenoxy or benzyloxy. A suitable alkanoyl is acetyl or propionyl. The benzyl group can have more than one ring substituent; examples of polysubstituted groups are those substituted with up the maximum possible number (especially 1, 2 or 3) of for example halogen (particularly chlorine) atoms and/or nitro, methyl or methoxy groups. Suitable substituents on the $CH_2$ moiety of the benzyl group are halogen, $C_{1-4}$ alkyl (e.g. methyl), phenyl or benzyl, both latter groups being optionally substituted as indicated above for benzyl, cyano, ($c_{1-4}$ alkoxy)carbonyl [e.g. methoxy- or ethoxycarbonyl] or trihalomethyl (e.g. trifluoromethyl).

$R_4$ can be benzyl itself, α-methylbenzyl, α-methylchlorobenzyl (e.g. α-methyl-p-chlorobenyl), α-methyldichlorobenzyl (e.g. α-methyl-2,4-dichlorobenzyl), α-methylbromobenzyl (e.g. α-methyl-p-bromobenzyl), α-methylfluorobenzyl [e.g. α-methyl-p-fluorobenzyl], α-ethylchlorobenzyl (e.g. α-ethyl-p-chlorobenzyl), α-ethylfluorobenzyl (e.g. α-ethyl-p-fluorobenzyl), chlorobenzyl (for example o-, m- or p-chloro-benzyl), dichlorobenzyl (e.g. 2,4-, 3,4- or 2,6-dichlorobenzyl), trichlorobenzyl (e.g. 2,3,6- or 2,4,5-trichlorobenzyl), tetrachlorobenzyl, pentachlorobenzyl, bromobenzyl (e.g. o-, m- or p-bromobenzyl), dibromobenzyl (e.g. 2,4-dibromobenzyl), fluorobenzyl (e.g. o-, m- or p-fluorobenzyl), difluorobenzyl (e.g. 2,4-difluorobenzyl), pentafluorobenzyl, iodobenzyl (e.g. o-iodobenzyl), aminobenzyl (e.g. p-aminobenzyl), methylbenzyl (e.g. o-, m- or p-methylbenzyl), dimethylbenzyl (e.g. 2,6-, 2,5- or 3,4-dimethylbenzyl), ethylbenzyl (e.g. p-ethylbenzyl), propylbenzyl (e.g. p-i-propylbenzyl), butylbenzyl (e.g. p-t-butylbenzyl), cyanobenzyl (e.g. o- or p-cyanobenzyl), hydroxybenzyl (e.g. p-hydroxybenzyl), nitrobenzyl (e.g. o-, m- or p-nitrobenzyl), (trifluoromethyl)benzyl [e.g. o-, m- or p-(trifluoromethyl)benzyl], methoxybenzyl (e.g. o-, m- or p-methoxybenzyl), ethoxybenzyl (e.g. o-, m- or p-ethoxybenzyl), chloronitrobenzyl (e.g. 3-nitro-4-chlorobenzyl), fluoronitrobenzyl (e.g. 2-nitro-4-fluorobenzyl), chlorofluorobenzyl e.g. 2-chloro-4-fluorobenzyl, 2-fluoro-4-chlorobenzyl or 2-chloro-6-fluorobenzyl), fluorobromobenzyl (e.g. 2-fluoro-4-bromo-benzyl), methylenedioxychlorobenzyl (e.g. 2-chloro-4,5-methylenedioxybenzyl), methoxybromobenzyl (e.g. 2-methoxy-5-bromobenzyl or 3-bromo-5-methoxybenzyl), methoxynitrobenzyl (e.g. 2-methoxy-5-nitrobenzyl), benzloxybenzyl (e.g. p-benzyloxybenzyl), phenylbenzyl (e.g. p-phenylbenzyl), phenylethyl (e.g. 2-phenylethyl), diphenylethyl or naphthylmethyl.

The cycloalkyl group suitably has 3 to 6 carbon atoms; preferably it is cyclopropyl, cyclopentyl or cyclohexyl.

A preferred class of compounds are those wherein $R_4$ is propenyl, phenylpropenyl, propynyl, benzyl, α-methylbenzyl, α-methylchlorobenzyl, α-methyldichlorobenzyl, α-methylfluorobenzyl, α-methylbromobenzyl, α-ethylchlorobenzyl, α-ethylfluorobenzyl, chlorobenzyl, dichlorobenzyl, trichlorobenzyl, pentachlorobenzyl, bromobenzyl, dibromobenzyl, fluorobenzyl, difluorobenzyl, iodobenzyl, aminobenzyl, methylbenzyl, dimethylbenzyl, ethylbenzyl, butylbenzyl, isopropylbenzyl, cyanobenzyl, hydroxybenzyl, nitrobenzyl, trifluoromethylbenzyl, methoxybenzyl, ethoxybenzyl, chloronitrobenzyl, fluoronitrobenzyl, chlorofluorobenzyl, fluorobromobenzyl, methylenedioxychlorobenzyl, methoxynitrobenzyl, phenylbenzyl, diphenylethyl or benzyloxybenzyl, $R_5$ is cyclohexyl, propyl or butyl and Z is C=O.

Particularly preferred are those compounds wherein R₄ is allyl, 3-phenylallyl, propargyl, benzyl, α-methylbenzyl, α-methyl-p-chlorobenzyl, α-methyl-2,4-dichlorobenzyl, α-methyl-p-bromobenzyl, α-methyl-p-fluorobenzyl, α-ethyl-p-chlorobenzyl, α-ethyl-p-fluorobenzyl, o-, m- or p-chlorobenzyl, 2,4-, 3,4- or 2,6-dichlorobenzyl, 2,4,5- or 2,3,6-trichlorobenzyl, pentachlorobenzyl, o-, m- or p-bromobenzyl, 2,4-dibromobenzyl, o-, m- or p-fluorobenzyl, 2,4-difluorobenzyl, o-iodobenzyl, p-aminobenzyl, o-, m- or p-methylbenzyl, 2,5- or 3,4-dimethylbenzyl, p-ethylbenzyl, p-t-butylbenzyl, o- or p-cyanobenzyl, o-, m- or p-nitrobenzyl, o-, m- or p-(trifluoromethyl)benzyl, o- or p-methoxybenzyl, o-, m- or p-ethoxybenzyl, 3-nitro-4-chlorobenzyl, 2-nitro-4-fluorobenzyl, 2-chloro-4-fluorobenzyl, 2-fluoro-4-chlorobenzyl, 2-chloro-6-fluorobenzyl, 2-fluoro-4-bromobenzyl, 2-chloro4,5-methylenedioxybenzyl, 3-bromo-5-methoxybenzyl, 2-methoxy-5-nitrobenzyl, p-benzyloxybenzyl, p-phenylbenzyl or β,β-diphenylethyl, R₅ is cyclohexyl, i-propyl, t-butyl or i-butyl and Z is C=O.

Suitable salts are salts with inorganic or organic acids, e.g. hydrochloric, nitric, sulphuric, toluenesulphonic, acetic or oxalic acid.

Specific examples of suitable triazole compounds are given in Table I.

TABLE I

| COMPOUND NO | R₄ | R₅ | Z | MELTING (OR BOILING) POINT °C. |
|---|---|---|---|---|
| 1 | p-Cl—C₆H₄CH₂— | t-Bu | C=O | 122–123° |
| 2 | CH₂CH=CH₂ | t-Bu | C=O | (130°/0.1 mm) |
| 3 | C₆H₅CH₂— | t-Bu | C=O | 69–70° |
| 4 | m-CH₃—C₆H₄CH₂— | t-Bu | C=O | 64–66° |
| 5 | p-NO₂—C₆H₄CH₂— | t-Bu | C=O | 140–142° |
| 6 | m-CF₃—C₆H₄CH₂ | t-Bu | C=O | 68–70° |
| 7 | p-F—C₆H₄CH₂ | t-Bu | C=O | |
| 8 | 3,4-diCl—C₆H₃CH₂ | t-Bu | C=O | 85–86° |
| 9 | p-CN—C₆H₄CH₂ | t-Bu | C=O | 122–125° |
| 10 | CH₂C≡CH | t-Bu | C=O | 83–85° |
| 11 | o-F—C₆H₄CH₂— | t-Bu | C=O | 84–86° |
| 12 | o-NO₂—C₆H₄CH₂— | t-Bu | C=O | 88–89° |
| 13 | 2,6-diCl—C₆H₃CH₂— | t-Bu | C=O | 130–132° |
| 14 | 2,4-diCl-C₆H₃CH₂— | t-Bu | C=O | 140–142° |
| 15 | p-Cl—C₆H₄CH₂ | i-Pr | C=O | 115–117° |
| 16 | 2-CH₃O—5-NO₂—C₆H₃CH₂— | t-Bu | C=O | 185–187° |
| 17 | C₆H₅CH₂— | i-Pr | C=O | 83–84° |
| 18 | o-Br—C₆H₄CH₂— | t-Bu | C=O | 76–77° |
| 19 | 3-NO₂—4-Cl—C₆H₃CH₂— | t-Bu | C=O | 100–102° |
| 20 | C₆H₅CH=CHCH₂— | t-Bu | C=O | 49–50° |
| 21 | 2-Cl-4,5-methylenedioxybenzyl | t-Bu | C=O | 127–129° |
| 22 | C₆H₅CH(CH₃)— | t-Bu | C=O | 86–89° |
| 23 | p-NO₂—C₆H₄CH₂— | i-Pr | C=O | 121–123° |
| 24 | p-F—C₆H₄CH₂ | i-Pr | C=O | 71–74° |
| 25 | p-CN—C₆H₄CH₂— | i-Pr | C=O | 117–119° |
| 26 | 3,4-diCl—C₆H₃CH₂— | i-Pr | C=O | 78–80° |
| 27 | p-Cl—C₆H₄CH₂— | cyclohexyl | C=O | 80–82° |
| 28 | p-Cl—C₆H₄CH(CH₃)— | t-Bu | C=O | 143–146° |
| 29 | 2-Cl—4-F—C₆H₃CH₂— | t-Bu | C=O | 102–103° |
| 30 | o-Cl—C₆H₄CH₂— | t-Bu | C=O | 86–88° |
| 31 | p-Br—C₆H₄CH₂— | t-Bu | C=O | 137–139° |
| 32 | m-F—C₆H₄CH₂ | t-Bu | C=O | 58–59° |
| 33 | m-Br—C₆H₄CH₂ | t-Bu | C=O | 86–88° |
| 34 | 2,4-diCl—C₆H₃CH₂ | i-Pr | C=O | 131–133° |
| 35 | p-C₆H₅—C₆H₄CH₂— | t-Bu | C=O | 111–113° |
| 36 | o-F—C₆H₄CH₂— | i-Pr | C=O | 77–78° |
| 37 | C₆Cl₅CH₂— | t-Bu | C=O | 188–190° |
| 38 | 2,4,5-triCl—C₆H₂CH₂— | t-Bu | C=O | 132–134° |
| 39 | 2,3,6-triCl—C₆H₂CH₂— | t-Bu | C=O | 111–113° |
| 40 | 2-F—4-Cl—C₆H₃CH₂— | t-Bu | C=O | 110–112° |
| 41 | 2,4-diF—C₆H₃CH₂ | t-Bu | C=O | 64–66° |
| 42 | p-F—C₆H₄CH(CH₃)— | t-Bu | C=O | 138–139° |
| 43+ | p-Cl—C₆H₄CH(C₂H₅)— | t-Bu | C=O | 92–94° |
| 44+ | p-F—C₆H₄CH(C₂H₅)— | t-Bu | C=O | 87–89° |
| 45 | p-Br—C₆H₄CH(CH₃)— | t-Bu | C=O | 144–146° |
| 46 | 2-F—4-Br—C₆H₃CH₂— | t-Bu | C=O | 126–128° |
| 47 | 2,4-diBr—C₆H₃CH₂— | t-Bu | C=O | 164–166° |
| 48 | o-CH₃O—C₆H₄CH₂ | t-Bu | C=O | 83–85° |

TABLE I-continued

| COMPOUND NO | R4 | R5 | Z | MELTING (OR BOILING) POINT °C. |
|---|---|---|---|---|
| 49 | o-CH$_3$—C$_6$H$_4$CH$_2$ | t-Bu | C=O | 73–75° |
| 50 | p-CH$_3$—C$_6$H$_4$CH$_2$ | t-Bu | C=O | 99–101° |
| 51 | 2,4-diCl—C$_6$H$_3$CH(CH$_3$)— | t-Bu | C=O | 94–96° |
| 52 | 2,5-diMe—C$_6$H$_3$CH$_2$ | t-Bu | C=O | 69–71° |
| 53 | p-C$_6$H$_5$CH$_2$O—C$_6$H$_4$CH$_2$ | t-Bu | C=O | 94–96° |
| 54 | C$_6$H$_5$CH(C$_6$H$_5$)CH$_2$ | t-Bu | C=O | 203–204° |
| 55 | p-Cl—C$_6$H$_4$CH$_2$ | t-Bu | C=O | 69–71° |
| 56 | 3-Br—5-MeO—C$_6$H$_3$CH$_2$ | t-Bu | C=O | 124–125° |
| 57 | p-MeO—C$_6$H$_4$CH$_2$ | t-Bu | C=O | 64–65° |
| 58 | p-EtO—C$_6$H$_4$CH$_2$ | t-Bu | C=O | 90–91° |
| 59 | o-EtO—C$_6$H$_4$CH$_2$ | t-Bu | C=O | — |
| 60 | 2-NO$_2$—4-F—C$_6$H$_3$CH$_2$ | t-Bu | C=O | 82–85° |
| 61 | p-NH$_2$C$_6$H$_4$CH$_2$ | t-Bu | C=O | 121–123° |
| 62 | o-CN—C$_6$H$_4$CH$_2$ | t-Bu | C=O | 110–113° |
| 63 | p-(t-Bu)—C$_6$H$_4$CH$_2$ | t-Bu | C=O | |
| 64 | o-I—C$_6$H$_4$CH$_2$ | t-Bu | C=O | 126–127° |
| 65 | p-Et—C$_6$H$_4$CH$_2$ | t-Bu | C=O | 100.5° |
| 66 | p-Cl—C$_6$H$_4$CH$_2$ | i-Bu | C=O | 79–81° |
| 67 | 2,4-diCl—C$_6$H$_3$CH$_2$ | i-Bu | C=O | 101–103° |
| 68 | p-F—C$_6$H$_4$CH$_2$ | i-Bu | C=O | 57–58° |
| 69 | m-NO$_2$—C$_6$H$_4$CH$_2$ | t-Bu | C=O | 117–119° |
| 70 | 2-Cl—6-F—C$_6$H$_3$CH$_2$ | t-Bu | C=O | 93–96° |
| 71 | p-CF$_3$—C$_6$H$_4$CH$_2$ | t-Bu | C=O | 105–107° |
| 72 | 2-Cl—4-F—C$_6$H$_3$CH$_2$ | i-Bu | C=O | 57–59° |
| 73 | o-CF$_3$—C$_6$H$_4$CH$_2$— | t-Bu | C=O | 114° |
| 74 | m-EtO—C$_6$H$_4$CH$_2$— | t-Bu | C=O | 59–60° |
| 75 | 3,4-diMe—C$_6$H$_3$CH$_2$— | t-Bu | C=O | 70–71° |
| 76 | H | t-Bu | C=O | 63–65° |
| 77 | n-Bu | t-Bu | C=O | 94–96° |
| 78 | p-(i-Pr)—C$_6$H$_4$CH$_2$ | t-Bu | C=O | 69° |
| 79 | o-CF$_3$—C$_6$H$_4$CH$_2$ | t-Bu | C=O | 114° |
| 80 | p-HO—C$_6$H$_4$CH$_2$ | t-Bu | C=O | 221–222° |
| 81 | C$_6$H$_5$CH$_2$ | i-Bu | C=O | 64–66° |
| 82 | p-Me—C$_6$H$_4$CH$_2$ | i-Bu | C=O | 63–65° |
| 83 | o-F—C$_6$H$_4$CH$_2$ | i-Bu | C=O | 61–63° |

The compounds may be made by reacting 1,2,4-triazole or a salt thereof with the appropriate activated halo compound (for example an α-haloketone, α-haloacid, α-haloester, α-haloamide or substituted alkyl halide) using methods set out in the literature. Thus 1,2,4-triazole, or a salt thereof, can be reacted with a compound of general formula (II):

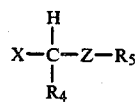

wherein X is halogen, preferably bromine or chlorine, and R$_4$, R$_5$ and Z are as defined above.

Alternatively, the compounds wherein R$_4$ is other than hydrogen can be made by hydrocarbylating (e.g. with an appropriately substituted alkylating or aralkylating agent) a compound of general formula (III):

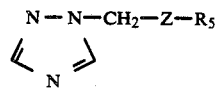

wherein Z, and R$_5$ are as defined above, or a salt thereof, suitably in the presence of a base in a hydroxylic or non-hydroxylic solvent using methods set out in the literature.

These processes may in some cases be carried out by heating the reactants together in the absence of a solvent or diluent, but preferably a solvent is present. Suitable solvents are non-hydroxylic solvents such as acetonitrile (which is preferred), dimethylformamide, dimethyl sulphoxide, sulpholane and tetrahydrofuran. Hydroxylated solvents, for example methanol and ethanol, may be used in certain circumstances when the presence of the hydroxyl group does not interfere with the progress of the reaction. The processes may also be carried out in the presence of a base, but preferably excess triazole is present to remove liberated HX from the reaction. Other suitable bases are sodium hydride (although not when a hydroxylated solvent or diluent is used), alkali metal carbonates (such as potassium hydroxide). The reaction temperature depends upon the choice of reactants, solvent and base, but generally the reaction mixture is refluxed.

The processes generally involve dissolving the reactants in a solvent and, after allowing reaction to occur, isolating the product by removal of the reactant solvent in vacuo.

The unreacted triazole is removed by extraction of the product with a suitable solvent and the extract is washed with water. A crystallisation or other purification procedure may then be carried out if desired.

The activated halo compounds may be made by any of the methods set out in the literature.

The compounds wherein Z is a derivative of C=O may be made from the respective carbonyl compound using any of the standard techniques set out in the literature.

The compounds are active fungicides, particularly against the following diseases:

*Piricularia oryzae* on rice

*Puccinia recondita* and other rusts on wheat and rusts on other hosts

*Plasmopara viticola* on vines

*Erysiphe graminis* (powdery mildew) on barely and wheat and other powdery mildews on various hosts such as *Sphaerotheca fulginea* on cucumbers, *Podosphaera leucotricha* on apples and *Uncinula necator* on vines

*Botrytis cinerea* (grey mould) on tomatoes, strawberries, vines and other hosts

*Gleosporiun musarum* on bananas and *Penicillium digitatum* on oranges (Compounds 8 and 19 show activity against these latter two)

Some of the compounds are active in the form of seed dressings against:

Fusarium spp., Septoria spp., Tilletia spp., and Pyrenophora spp. on cereals.

The compounds also have certain anti-bacterial and anti-viral activities.

They may be used as such for anti-fungal purposes but are more conveniently formulated into compositions for such usage.

The invention therefore also provides a fungicidal composition comprising, as an active ingredient, a triazole compound or salt thereof, and a carrier for the active ingredient.

The invention also provides a method for combating pests, which are fungi, viruses or bacteria, which method comprises treating plants, seeds or trees with a triazole compound or salt thereof as hereinbefore defined.

The plant growth regulating effects of the compounds are manifested as, for example, by a stunting or dwarfing effect on the vegetative growth of woody and herbaceous mono- and di-cotyledonous plants. Such stunting or dwarfing may be useful in a wide variety of applications outlined below, although it is to be understood that the compounds of the invention will not necessarily be active against all species or have utility for every application listed. For example, in peanuts, cereals such as wheat and barley, oil seed rape, field beans, sunflowers, potatoes and soya bean reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agrostis tenuis, Cynodon dactylon* (Bermuda grass), *Dactylis glomerata, Festuca* spp. (e.g. *Festuca rubra*) and Poa spp. (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in, for example, grasses. The compounds can also stunt weed species present in the grasses; examples of such weed species are sedges (eg. Cyperus spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful, for example, for improving the quality of a sward by preferential suppression of the growth of undesirable species.

The dwarfing may also be useful in miniaturising ornamental, household, garden and nursery plants (e.g. poinsettias, chrysanthemums, carnations, tulips and daffodils).

As indicated above, the compounds can also be used to stunt woody species. This property can be used to control hedgerows or to shape or reduce the need for pruning, of fruit trees (e.g. apples, pears, cherries, peaches, vines etc). Some coniferous trees are not significantly stunted by the compounds so the compounds could be useful in controlling undesirable vegetation in conifer nurseries.

The plant growth regulating effect may (as implied above) manifest itself in an increase in crop yield; or in an ability in orchards and other crops to increase fruit set, pod set and grain set.

In the potato, vine control in the field and inhibition of sprouting in the store may be possible.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, e.g. wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (e.g. rice), the number of flowering shoots per unit area may be increased thereby increasing the overall grain yield of such crops. In addition better control and modification of hierarchical relationships is possible in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such a way as to increase yield. In the treatment of rice plants, or rice crops the invention compounds can be applied, e.g. as granules or a granular formulation, for example as slow release granules, to nursery boxes, paddy water and other like cultivation loci and media. In grass swards, especially amenity grass, an increase in tillering could lead to a denser sward which may result in increased resilience in wear; and to increased yields and better quality of forage grass, e.g. improved digestability and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (i.e. the harvested yield as a proportion of the total dry matter produced) by altering dry matter partitioning. This applies to all the aforementioned root, pod, cereal, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

The compounds can be used to combat plant pests and treat plants or seeds to provide plant growth regulating or other effects in a number of ways. For example they can be applied, formulated or unformulated, directly to the foilage of a plant which is infected or likely to become infected, or they can be applied also to bushes and trees, to seeds or to other medium in which plants, bushes or trees are growing or are to be planted, or they can be sprayed on, dusted on or applied as a cream or paste formulation. Application can be to any part of the plant, bush or tree, for example to the foliage, stems, branches or roots, or to soil surrounding the roots.

The term "treating" as used herein refers to all these modes of application and the term "plant" includes seedlings, bushes and trees. Furthermore, the method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered mangesia, Fuller's earth, gypsum, Hewitt's earth, diatomaceous earth and China clay. Compositions for dressing seed, for example, may comprise an agent (for example a mineral oil) for assisting the adhesion of the composition to the seed.

The compositions may also be in the form of dispersible powders or grains comprising a wetting agent to facilitate the dispersion in liquids of the powder of grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable solvents are ethylene dichloride, isopropyl alcohol, propylene glycol, diazetone alcohol, toluene, kerosene, methylnaphthalene, the xylenes and trichloroethylene.

The compositions to be used as sprays may also be in the form of aerosols wherein the formulation is held in a container under pressure in the present of a propellant, e.g. fluorotrichloromethane of dichlorodifluoromethane.

By including suitable additives, for example additives for improving the distribution, adhesive power and resistance to rain on treated surfaces, the different compositions can be better adapted for various utilities.

The compounds can be used as mixture with fertilisers (e.g. nitrogen—or phosphorus—containing fertilisers). Compositions comprising only granules of fertiliser incorporating, for example coated with, the triazole compound are preferred. The invention therefore also provides a fertiliser composition comprising the triazole compound.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or non-anionic agents.

Suitable cationic agents are quaternary ammonium compounds for example, cetyltrimethylammonium bromide. Suitable anionic agents are soaps, salts of aliphatic monoesters or sulphuric acid (for example sodium lauryl sulphate), and salts or sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates). Suitable non-ionic agents are the condensation products of ehtylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcel-lulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10–85%, generally 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, as well as stabilising agent(s), for example epoxides (e.g. epichlorhydrin).

In addition to being active as fungicides and plant growth regulators in their own right, certain compounds of the invention are useful as intermediates in the preparation of other agrochemicals. Thus for example in U.S. Pat. No. 4,243,405 there are disclosed fungicides and plant growth regulating compounds having the general formula:

$$Y-N-\underset{R^1}{\underset{|}{C}}-\underset{R^3}{\underset{|}{C}}-R_2$$

wherein inter alia Y is =N—, $R_1$ is optionally substituted aralkyl, for example halo-substitited benzyl, $R^3$ is hydrogen, and $R_2$ may be alkyl, for example teriary butyl. The specification discloses that such compounds may be prepared by reducing, preferably at 0° to 100° C. and for 1 to 12 hours, a compound of formula:

$$Y-N-\underset{R^1}{\underset{|}{C}}-\underset{O}{\underset{\|}{C}}-R_2$$

wherein Y, $R^1$ and $R^2$ are as defined above.

The following examples illustrate the invention; the temperatures are given in degrees Centigrade (°C.).

EXAMPLE 1

Alpha-1,2,4-Triazole-1-yl-pinacolone (Compound 1)

1,2,4-Triazole (33.4g) and sodium ethoxide [from sodium (11.6g) and ethyl alcohol (250 ml)] were refluxed for 1 hour. To this solution at the reflux temperature was added bromopinacolone (87 g), and the mixture was then heated for 2 hours. It was then cooled to ambient temperature and filtered to remove the precipitated sodium bromide; the solvent was removed in vacuo. The residue was extracted with chloroform (100 ml). The extract was washed with water (4×15 ml), died (sodium sulphate) and filtered. Petroleum ether (50 ml; b.p. 60°-80°) was added and the solution concentrated to give alpha-1,2,4-triazol-4-yl-pinacolone, m.p. 176°. Further concentration of the solution gave the title compund, m.p. 63°-65°.

EXAMPLE 2

α-p-Chlorobenzyl-60-1,2,4-triazol-1-yl-pinacolone (compound 2)

α-1,2,4-Triazol-1-yl-pinacolone (3.3 g in dimethylformamide (20 ml) was added dropwise to a suspension of sodium hydride (0.48 g; 100%) in dimethylformamide (10 ml) at room temperature with stirring. After stirring for two hours, p-chlorobenzyl chloride (3.2 g) in dimethylformamide (2-3 ml) was added dropwise and the reaction mixture was kept at 5°-10° for two hours. The solvent was removed in vacuo and water was added to the residue. The aqueous solution was extracted with methylene chloride, the organic layer was washed with water and dried (magnesium sulphate). The solvent was removed to give a yellow solid which was crystallised to give the title compound.

EXAMPLE 3

The compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots. Vermiculite was used to cover the seed in the soil tests.

The test compounds were formulated either by bead-milling with aqueous Dispersol T or as a solution in acetone/ethanol which was diluted to the required concentration immediately before use. For the foliage diseases, 100 p.p.m. a.i. suspensions were sprayed onto the foliage and applied to the roots of the same plant via the soil. (Sprays were applied to maximum retention, and root drenches to a final concentration equivalent to approximately 40 p.p.m. a.i./dry soil). Tween 20, to give a final concentration of 0.1%, was added when the sprays were applied to the cereals.

For most of the tests, the test compound was applied to the soil and foilage one or two days before the plant was inoculated with the diseases. An exception was the test on *Erysiphe graminis*, in which the plants were inoculated 24 hours before treatment. After inoculation, the plants were put into an appropriate environment to allow infection to take place and the incubated until the disease was ready for assessment. The period between inoculation and assessment varied from 3 to 10 days according to the disease and environment.

The disease control was recorded by following grading:

4=No disease
=0-5%
2=6-25%
1=26-60%
0=>60%

The results are shown in Table II.

TABLE II

| COMPOUND NUMBER | PUCCINIA RECONDITA (WHEAT) | PHYTOPHTHORA INFESTANS (TOMATO) | PLASMOPARA VITICOLA (VINE) | PIRICULARIA ORYZAE (RICE) | BOTRYTIS CINEREA (TOMATO) | ERYSIPHE GRAMINIS (BARLEY) |
|---|---|---|---|---|---|---|
| 1 | 3 | 0 | 0 | 0 | 3 | 4 |
| 2 | 3 | 3 |   | 0 | 0 | 4 |
| 3 | 3 |   |   | 2 |   | 4 |
| 4 | 2 | 3 |   | 2 |   | 3 |
| 5 | 4 | 1 |   | 0 |   | 4 |
| 6 | 2 | 3 |   | 1 | 1 | 4 |
| 7 | 3 |   | 0 | 1 | 1 | 4 |

TABLE II-continued

| COMPOUND NUMBER | PUCCINIA RECONDITA (WHEAT) | PHYTOPHTHORA INFESTANS (TOMATO) | PLASMOPARA VITICOLA (VINE) | PIRICULARIA ORYZAE (RICE) | BOTRYTIS CINEREA (TOMATO) | ERYSIPHE GRAMINIS (BARLEY) |
|---|---|---|---|---|---|---|
| 8 | 2 | | 2 | 0 | 3 | 4 |
| 9 | 4 | 0 | 0 | 0 | 0 | 4 |
| 10 | 3 | 0 | 0 | 0 | 0 | 4 |
| 11 | 3 | 0 | 0 | 1 | 3 | 4 |
| 12 | 1 | 1 | 0 | | 0 | 4 |
| 13 | 1 | 1 | 0 | | 2 | 3 |
| 14 | 1 | 0 | 0 | 0 | 3 | 4 |
| 15 | 4 | 0 | 3 | 0 | 0 | 4 |
| 16 | 0 | 0 | 0 | 0 | 0 | 0 |
| 17 | 3 | 1 | 0 | 0 | 1 | 4 |
| 18 | 1 | 0 | 0 | 0 | 2 | 4 |
| 19 | 1 | 0 | 0 | 1 | 0 | 4 |
| 20 | 3 | 0 | 0 | 0 | 2 | 4 |
| 21 | 0 | 0 | 0 | 0 | 1 | 4 |
| 22 | 3 | | 0 | 0 | 2 | 4 |
| 23 | 3 | 0 | 0 | 0 | 0 | 4 |
| 24 | 3 | 0 | 0 | | 0 | 4 |
| 25 | 3 | 0 | 0 | 1 | 0 | 4 |
| 26 | 1 | 1 | 0 | 1 | 0 | 4 |
| 27 | 4 | 0 | 0 | 1 | 0 | 4 |
| 28 | 3 | 1 | 0 | 1 | 3 | 4 |
| 29 | 3 | 0 | 0 | 0 | 3 | 4 |
| 30 | 3 | 0 | 0 | 0 | 3 | 4 |
| 31 | 3 | 0 | | 2 | 0 | 3 |
| 32 | 4 | 2 | 0 | 0 | 0 | 3 |
| 33 | 1 | 0 | 0 | 1 | 3 | 4 |
| 34 | 3 | 0 | 0 | 1 | 1 | 4 |
| 35 | 4 | 0 | 0 | 1 | 2 | 4 |
| 36 | 4 | 0 | 0 | | 2 | 4 |
| 37 | 0 | 0 | 0 | 2 | 0 | 4 |
| 38 | 0 | 0 | 0 | 0 | 3 | 4 |
| 39 | 1 | 0 | 0 | 0 | 2 | 2 |
| 40 | 3 | 1 | 0 | 0 | 3 | 4 |
| 41 | 3 | 0 | 3 | | 2 | 3 |
| 42 | 3 | 0 | 3 | 2 | 4 | 4 |
| 43 | 0 | 0 | 0 | 0 | 2 | 4 |
| 44 | 0 | 0 | 0 | 1 | 1 | 4 |
| 45 | 0 | 0 | 0 | 0 | 3 | 4 |
| 46 | 1 | 0 | 0 | 0 | 3 | 3 |
| 47 | 0 | 0 | 0 | 0 | 1 | 3 |
| 48 | 0 | 0 | 0 | 0 | 0 | 4 |
| 49 | 4 | 0 | 0 | 0 | 4 | 4 |
| 50 | 0 | 0 | 0 | 0 | 3 | 4 |
| 51 | 2 | 1 | 0 | 2 | 2 | 3 |
| 52 | 0 | 0 | 0 | 1 | 4 | 4 |
| 53 | 0 | 2 | | 0 | 2 | 4 |
| 54 | 0 | 0 | 0 | 0 | 0 | 2 |
| 55 | 4 | 2 | 2 | 2 | 2 | 4 |
| 56 | 1 | 0 | | | 4 | 3 |
| 57 | 1 | 2 | 0 | 3 | 2 | 4 |
| 58 | 0 | 1 | 0 | 0 | 4 | 4 |
| 59 | 0 | 0 | 0 | 3 | 3 | 4 |
| 60 | 4 | 3 | 0 | 1 | 0 | 4 |
| 61 | 1 | 0 | 0 | 0 | | 3 |
| 62 | 1 | 0 | 0 | 0 | 3 | 4 |
| 64 | 3 | 2 | | 0 | 1 | 4 |
| 65 | 0 | 0 | 0 | 0 | 0 | 4 |
| 66 | 4 | 0 | | 1 | 0 | 4 |
| 67 | 3 | 0 | | 3 | 0 | 4 |
| 68 | 4 | | | 3 | 4 | 4 |
| 69 | 2 | 0 | 0 | 1 | 0 | 4 |
| 70 | 3 | 0 | 0 | 0 | 3 | 4 |
| 71 | 3 | 3 | 0 | 2 | 2 | 3 |
| 72 | 4 | 0 | 0 | 1 | 2 | 4 |
| 76 | 1 | 3 | 0 | 0 | 0 | 4 |
| 77 | 4 | 0 | | 1 | 3 | 4 |

EXAMPLE 4

This example illustrates the plant growth regulatory properties of Compound Nos. 1, 3 and 14 in Table I.

Methodology

Three species of grass were grown in plastic punnets, a row of each specie. Species included were *Agrostis tenuis*, *Cynosurus cristatus*, and *Dactylis glomerata*. These are examples of fine leaved, medium leaved and broad leaved grasses.

Each compound was tested at 4 rates 1, 2, 4 and 8 kg/ha corresponding to 1,2,4 and 8000 ppm. There were five replicates per treatment.

Each species was assessed for retardation greening and phytotoxicity. Scoring for retardation was done on a 0-5 scale where:

0=no reduction in height compared to controls

5=100% reduction in height i.e. no increase in height from spray

Phytotoxicity was also scored on a 0–5 scale where:
0=no phytotoxicity
5=completely killed "Greeness" was scored on a 0–3 scale where:
0=same colour as control
3=very much darker green Results The scores for each species were added up and totalled over 5 replicates giving a maximum possible value of 75 for retardation and phytotoxicity and 45 for greeness. The results are shown in Table III.

TABLE III

| Compound No | Retardation (out of 75) | Greening (out of 45) | Phyto (out of 75) | Rate kg/ha |
| --- | --- | --- | --- | --- |
| 3 | 14 | 21 | 0 | 1 |
|   | 9 | 14 | 0 | 2 |
|   | 19 | 24 | 4 | 4 |
|   | 10 | 28 | 4 | 8 |
| 1 | 16 | 25 | 0 | 1 |
|   | 11 | 24 | 0 | 2 |
|   | 7 | 42 | 0 | 4 |
|   | 19 | 27 | 0 | 8 |

TABLE III-continued

| Compound No | Retardation (out of 75) | Greening (out of 45) | Phyto (out of 75) | Rate kg/ha |
| --- | --- | --- | --- | --- |
| 14 | 8 | 13 | 0 | 1 |
|   | 7 | 16 | 0 | 2 |
|   | 13 | 15 | 0 | 4 |
|   | 21 | 20 | 3 | 8 |

We claim:

1. A compound of the formula:

$$N\!=\!\!\!\overset{\|}{\underset{N}{\diagdown}}\!\!\!N\!-\!\!\overset{H}{\underset{R_4}{\overset{|}{C}}}\!-\!Z\!-\!R_5$$

wherein $R_4$ is benzyl or benzyl ring-substituted with halogen, $R_5$ is t-butyl, and Z is C=O or C=NH, or a salt of said compound.

2. A compound according to claim 1, wherein $R_4$ is benzyl substituted with chlorine and $R_5$ is t-butyl.

3. A compound according to claim 1 wherein $R_4$ is para-chlorobenzyl, $R_5$ is t-butyl and Z is C=O.

4. A compound according to claim 1 wherein $R_4$ is benzyl, $R_5$ is t-butyl and Z is C=O.

5. A compound according to claim 1 wherein $R_4$ is 2,4-dichlorobenzyl, $R_5$ is t-butyl and Z is C=O.

* * * * *